(12) United States Patent
Brownscombe

(10) Patent No.: US 6,441,225 B1
(45) Date of Patent: Aug. 27, 2002

(54) PURIFICATION OF AROMATIC DIACIDS

(75) Inventor: Thomas Fairchild Brownscombe, Houston, TX (US)

(73) Assignee: Mossi & Ghisolfi Overseas, S.A. (LU)

( * ) Notice: Subject to any disclaimer, the term of this patent is extended or adjusted under 35 U.S.C. 154(b) by 0 days.

(21) Appl. No.: 09/643,587

(22) Filed: Aug. 22, 2000

Related U.S. Application Data

(60) Provisional application No. 60/151,578, filed on Aug. 30, 1999, provisional application No. 60/151,577, filed on Aug. 30, 1999, provisional application No. 60/151,607, filed on Aug. 30, 1999, provisional application No. 60/151,498, filed on Aug. 30, 1999, provisional application No. 60/151,602, filed on Aug. 30, 1999, provisional application No. 60/151,603, filed on Aug. 30, 1999, provisional application No. 60/151,529, filed on Aug. 30, 1999, provisional application No. 60/151,489, filed on Aug. 30, 1999, provisional application No. 60/151,604, filed on Aug. 30, 1999, provisional application No. 60/151,606, filed on Aug. 30, 1999, provisional application No. 60/151,589, filed on Aug. 30, 1999, provisional application No. 60/151,497, filed on Aug. 30, 1999, and provisional application No. 60/151,590, filed on Aug. 30, 1999.

(51) Int. Cl.[7] ............................................... C07C 51/42
(52) U.S. Cl. ........................ 562/485; 562/486; 562/494
(58) Field of Search ................................ 562/481, 485, 562/486, 494

(56) References Cited

U.S. PATENT DOCUMENTS

| 2,891,992 | A | | 6/1959 | Raecke et al. |
| 2,905,709 | A | | 9/1959 | Schenke et al. |
| 2,927,130 | A | * | 3/1960 | Schutt et al. |
| 3,671,578 | A | * | 6/1972 | Ogata et al. |
| 5,859,294 | A | * | 1/1999 | Hashimoto |
| 6,194,607 | B1 | * | 2/2001 | Jhung et al. |

FOREIGN PATENT DOCUMENTS

| JP | 357212138 A | * | 12/1982 |
| JP | 406184044 A | * | 7/1994 |

* cited by examiner

Primary Examiner—Paul J. Killos
Assistant Examiner—Zachary Tucker
(74) Attorney, Agent, or Firm—Renner, Kenner, Greive, Bobak, Taylor & Weber

(57) ABSTRACT

A method is provided to produce dicarboxylic or tricarboxylic aromatic acid from salts of such acids, the method including the steps of providing an aqueous solution of a salt of a dicarboxylic or tricarboxylic aromatic acid, the aqueous solution having a pH of about 7 or greater; contacting the aqueous solution with sufficient carbon dioxide to lower the pH of the aqueous solution resulting in precipitation of at least a portion of the dicarboxylic or tricarboxylic aromatic acid; separating precipitated dicarboxylic or tricarboxylic aromatic acid from the solution; and recovering carbon dioxide from the solution.

18 Claims, No Drawings

PURIFICATION OF AROMATIC DIACIDS

CROSS REFERENCE

This application claims the benefit of U.S. application Ser. Nos. 60/151,578, 60/151,577, 60/151,607, 60/151,498, 60/151,602, 60/151,603, 60/151,529, 60/151,489, 60/151, 604, 60/151,606, 60/151,589, 60/151,497, and 60/151,590 filed of even date, Aug. 30, 1999, and incorporated by reference herein.

FIELD OF THE INVENTION

This invention relates to a method to recover and purify aromatic diacids.

BACKGROUND TO THE INVENTION

Terephthalic acid is typically produced by oxidation of paraxylenes and then separation of the oxidized paraxylenes by precipitation, and then washing the precipitate to remove trace solvents.

In a process that is not currently commercially utilized, it is known to isomerize aromatic carboxylic acids to terephthalic acids utilizing a solid state isomerization of salts of the aromatic carboxylic acids in the presence of carbon dioxide and salts such as potassium carbonate or cadmium fluoride, as disclosed in, for example, U.S. Pat. No. 2,891,992. This process results in solid salts that still must be purified and changed from the salt to the diacid. Mineral acids in aqueous solutions have been used to acidify the salts. The dicarboxylic acids are significantly less soluble in aqueous solutions than the corresponding salts, and they therefore readily precipitate from the solution upon acidization or upon acidization and cooling. Acidification of the aromatic dicarboxylic acid salts with mineral acids results in a solvent stream that contains the salt of the mineral acid. These streams can generally not be reused in the process, and must therefore be disposed of.

A process wherein salts resulting from the acidification step could be recycled would be preferable. U.S. Pat. No. 2,905,709 suggests such a process. The process of '709 involves providing an aqueous solution of a salt of terephthalic acid, and acidifying the solution with an aromatic acid. The aromatic acid can be readily recovered and recycled, but use of the aromatic acid has other disadvantages. Trace amounts of the aromatic acid which are in the terephthalic acid precipitate must be removed to obtain a composition useful for polymerization because the aromatic acids are chain terminators in polymerization. It would therefore be desirable to have a process wherein salts resulting from the acidification step could be recycled, but which would not introduce a compound which acts as a chain terminator.

It is therefore an object of the present invention to provide a process to acidify and precipitate carboxylic diacids in a process wherein a waste stream containing salts of a mineral acid is not produced.

SUMMARY OF THE INVENTION

This and other objects are accomplished by a method to produce dicarboxylic or tricarboxylic aromatic acid from salts of such acids, the method comprising the steps of providing an aqueous solution of a salt of a dicarboxylic or tricarboxylic aromatic acid, the aqueous solution having a pH of about 7 or greater; contacting the aqueous solution with sufficient carbon dioxide to lower the pH of the aqueous solution, resulting in precipitation of the dicarboxylic or tricarboxylic aromatic acid; separating precipitated dicarboxylic or tricarboxylic aromatic acid from the solution; and recovering carbon dioxide from the solution until the pH of the solution is at least about 7.

The aqueous solution remaining after terephthalic acid is precipitated contains salts of carboxylic acid, such as potassium carboxylate. Carbon dioxide can therefore be recovered from this solution by heating the solution. The remaining solution would be of a high pH, and could be used to generate an aqueous solution of the salt of the terephthalic acid.

It has also been found that contact of precipitated aromatic diacids which contain monosalts of the diacids can be disproportioned to disalts and diacids by contact with water. Further, when the desired diacid is not the least soluble species present (for example, when isophthalic acid is being produced and terephthalic acid is present), the less soluble species can be precipitated first, and then the more soluble species, thus providing a solid of the less soluble species.

DESCRIPTION OF A PREFERRED EMBODIMENT

The present invention may be utilized to recover a wide variety of dicarboxylic and tricarboxylic aromatic acids from solutions of salts of such acids. The preferred dicarboxylic and tricarboxylic acids include terephthalic acid, phthalic acid, trimesic acid, isophathalic acid, and naphthalene dicarboxylate acid. Particularly preferred are terephthalic acid and 2, 6 naphthalene dicarboxylic acid, based on their low solubilities and high commercial value. Other one or two aromatic ring compounds containing two or three acid groups, and mixtures thereof, can be prepared from salts of the acids.

The starting material of the present invention is preferably a Henkle reaction product, or the dicarboxylic acid salt of an aromatic or naphthalene that has been isomerized by contact at temperatures of above about 300° C. with salts under carbon dioxide pressure. Such reaction products are in a salt state, and are generally subsequently converted to diacids and separated from more soluble salt byproducts. Such salts can be dissolved in water, and then contacted with carbon dioxide according to the present invention in order to acidify and separate desirable products.

The first $pK_a$ of carbonic acid is 6.35, and the second is 10.33. Thus, there is a gap of almost 3, or almost 1000 in equilibrium constant terms between the acidity of carbonic acid and the strong acid group of dicarboxylic aromatic acids. It is therefore unexpected that carbon dioxide, at reasonable partial pressures, could be useful to participate the dicarboxylic aromatic acids according to the present invention. Additionally, the carbon dioxide can be readily recycled, reducing the costs of the materials and reducing environmental discharges.

To provide sufficient carbonic acid in solution, the final temperature, during precipitation of the dicarboxylic or tricarboxylic aromatic acid is less than about 150° C., and preferably between about 0° C. and about 100° C. The partial pressure of carbon dioxide is preferably between about 15 and about 1000 psi, and most preferably between about 700 and about 1000 psi, depending on the temperature, concentration of acid and the composition of the salt solution. The optimum pressure depends on the $pK_a$ of the acid to be precipitated, the concentration of the acid salt, the fraction of salt required to be converted to the acid, and other factors such as the expense of providing equipment capable of higher pressures.

The precipitate could be at least in part a monosalt, in which case the precipitate could be washed with water to disproportionate the monosalt into disalts and diacids. The disalts could then be removed by the water wash. At higher concentrations of the dicarboxylic or tricarboxylic acid salts, the precipitate will contain a significant portion of monosalts, thus the water wash and disproportionation is preferred when the concentration of the dicarboxylic or tricarboxylic acid salts are greater than about five percent.

It has also been found to be advantageous to perform two stages of contacting solutions of the dicarboxylic or tricarboxylic aromatic acid salts with carbon dioxide.

Crystals of precipitated dicarboxylic or tricarboxylic acids can be readily removed from the mother liquor by filtration, centrifugation, or gravity settling. These crystals may then be washed with water, preferably hot water, or solvents such as acetic acid to remove impurities.

The method of the present invention is most applicable to the least soluble product present in the product mixture, although more soluble products may be recovered by sequential differential precipitation as for example by raising the carbon dioxide pressure, collecting a crop of the least soluble acid, raising the carbon dioxide pressure or lowering the temperature to collect a crop of the more soluble acids, etc.

Carbon dioxide can be easily recovered from the solution by flashing off at a lower temperature, or by heating the liquid, or by a combination of the preceding. It is preferably that enough carbon dioxide be removed so that the liquid returns to a pH of greater than about 7, and preferably greater than about 9. The pH of the remaining liquid after removal of the carbon dioxide is preferably sufficiently high that the remaining liquid could be recycled to provide a basic solution for preparation of salts of the dicarboxylic acid. Carbon dioxide can be compressed, and recycled to the solution of a salt of a dicarboxylic or tricarboxylic aromatic acid to acidify the salt, and cause precipitation of the dicarboxylic or tricarboxylic acid.

EXAMPLES

Example 1

Potassium salt of terephthalic acid, in an amount of 0.31 grams was dissolved in 39 grams of water. Pure carbon dioxide was then bubbled through the solution (at ambient temperature) until the pH had lowered to about 6 (its equilibrium value). No precipitate was visible in this solution. The liquid was then split into two vials, each containing an equal amount of the solution.

Three drops of concentrated hydrochloric acid were added to one vial. Addition of concentrated hydrochloric acid lowered the pH to about 3, and terephthalic acid quickly precipitated.

A piece of dry ice was added to the second vial. The dry ice began to sublime, cooling the solution. As the temperature of the solution fell below about 15° C., precipitate began to form. At a temperature between about 5° C. and 10° C., the vial was filled with flocculent precipitate of appearance identical to that of the precipitate from the first vial (after addition of hydrochloric acid). The terephthalic acid recovered from the second vial was less than the amount of amount of recovered from the first vial, with about one third of the terephthalic acid present in the second vial recovered, and almost all of the terephthalic acid recovered from the first vial.

Example 2

0.22 grams of a potassium salt of terephthalate was dissolved in 10.5 grams of deionized water in a 20 ml vial, and 5 grams of dry ice was added directly, and the vial was loosely capped. After two to three minutes, the solution became cloudy, and soon a large quantity of flocculent terephthalic acid precipitate was formed. After filtration, about 40% of the theoretical yield of terephthalic acid was recovered. The filtrate was a clear solution of potassium salts. The pH increased from about 6 when chilled before filtration to about 7 after the dry ice had all sublimed, and the solution warmed to room temperature, showing the presence of excess base after the $CO_2$ had outgassed.

Example 3

Two grams of a dipotassium salt of 2,6 naphthalene dicarboxylic acid ("NDA") was dissolved in 60 grams of water along with one gram of a mixture of 2,3 naphthalene dicarboxylic acid, 1,4 naphthalene dicarboxylic acid, and enough $K_2CO_3$ to form a 5% molar excess of base. This mixture was charged into a 100 cc autoclave with a dip tube, magnetic stir bar, and a band heater. The autoclave was then pressured to 800 psig with carbon dioxide, heated to 80° C., and stirred for 20 minutes. At that time, the autoclave was vented out of the dip tube through a 10 micron in line filter followed by a 0.3 micron filter, to separate precipitated solid from the liquid filtrate. The precipitated solid was acid (pH less than 7) and the filtrate, after degassing of $CO_2$, was basic (pH greater than 7).

The precipitated solid contained greater than 75% of the NDA originally charged, and analysis by nuclear magnetic resonance spectroscopy showed the solid was 100% the 2,6 isomer of NDA. The 1,4 and 2,3 isomers were quantitatively recovered in the filtrate.

Elemental analysis of the solid precipitate by X-ray fluorescence showed the material to be grater than 70 percent of the NDA in the acid form, and less than 30 percent as the mono potassium salt of the 2,6 isomer of NDA.

The mono potassium salt of 2,6 NDA could be disproportionated by heating in water to form the diacid of 2,6 NDA and the dipotassium salt, the remaining 30 percent of monopotassium 2,6 NDA can be converted to 2,6 NDA plus the dipotassium salt by, for example, washing the monosalt with hot Water.

The precipitated solid was washed with a dilute solution of oxalic acid, which resulted in greater than 99 percent purity of the 2,6 NDA, substantially eliminating the monopotassium salt in the product without the use of mineral acid or insoluble organic acids which may contaminate the product.

Example 4

2.3 grams of the dipotassium salt of 2,6 naphthalene dicarboxylic acid was dissolved in 60 cc of water and placed in a 100 cc autoclave with a dip tube and stirrer. The autoclave was then flushed with carbon dioxide, pressured to 700 psig with carbon dioxide, depressured and opened. The effervescent contents were poured into a conventional glass gravity filter with a #3 filter paper and filtered. During the filtration process, most of the precipitate redissolved. This demonstrates that the filtration must be accomplished under a carbon dioxide pressure or the acids will shift back to the salt form and go back into solution.

Example 5

A autoclave was charged with a solution as in Example 4, and pressured to 700 psig with carbon dioxide, stirred for about 30 minutes, and then vented through the dip tube while still under carbon dioxide pressure. The solids were collected in an in-line 0.5 micron Nupro steel filter. Recovery of the naphthalate was about 90% of the naphthalate present. The recovered naphthalate was primarily the monopotassium 2,6 naphthalene dicarboxylic acid salt, with a small amount of the diacid.

Example 6

Example 5 was repeated with the autoclave heated to about 70° C., and depressured via the dip tube through the in-line filter. More than 80% of the naphthalate was recovered as above, except that the majority of the recovered material was in the diacid form, and a minority was in the monopotassium salt form. The recovered solids were washed with water, and the solids then contained 1000 ppm by weight or less potassium.

Example 7

The procedure of Example 6 was repeated at various temperatures and pressures. The yield of naphthalene diacid exceeded that of the disproportionation of the monopotassium salt to the disalt and diacid by varying amounts, with the yield exceeding that of the disproportionation by 30% at about 80° C. Different temperatures and pressures of carbon dioxide will be preferred for different salt mixtures and conditions, and these conditions will be readily determined by routine experimentation.

Example 8

The procedure of Example 6 was repeated with the addition of 2.3 grams of a mixture of roughly equal parts of the dipotassium salts of 2,3 and 1,4 naphthalene dicarboxylic acids. Upon pressure filtration, more than 80% of the 2,6 naphthalene dicarboxylic acid in the slurry was recovered in the in-line filter. A majority of the 2,6 naphthalene dicarboxylic acid recovered was in the acid form. Analysis of the recovered material by LC and NMR demonstrated the recovered solids contained greater than 99.9% of the 2,6 isomer. The filtrate liquid was similarly analyzed and determined to be greater than 80% 2,3 and 1,4 isomers in the salt form. A majority of the remaining naphthalene dicarboxylic acid was the 2,6 isomer in the salt form. This demonstrates that the method of the present invention can produce a product of high isomeric purity, with a majority of the recovered produce in the acid form when the first isomer to crystalize is recovered, with the remaining isomers remaining in the salt form.

Example 9

The procedure of Example 8 was repeated in which the impurity was dipotassium terephthalate. More than 90% of the terephthalate remained in solution at between about 60° C. and 80° C., while the majority of the 2,6 naphthalene dicarboxylic acid was recovered as precipitate.

Example 10

A 15.2% by weight solution of the potassium salt of NDA ("K2NDA") was prepared by mixing 34.8 mmoles of 2,6 NDA and 69.6 mmoles of KOH in water. The pH of this solution was 12.9. The solution was contacted with $CO_2$ at 700 psig and 100° C. for one hour with stirring. The pressure was then reduced to atmospheric, and the solution filtered quickly. The solids collected contained 24.9 mmoles of the monopotassium salt of NDA ("KHNDA") and 1.3 mmoles of NDA. This is equivalent to a 75% molar conversion and 5% acid purity. The filtrate recovered from this experiment had a pH of 8.3.

Example 11

A similar 15.2% by weight solution was contacted with $CO_2$ at 700 psig and 25° C. in two steps. The first contact step lasted one hour and the second one 20 minutes. After each step, the pressure was reduced and the solution filtered. The product collected upon filtration after the first contact step corresponded to a molar conversion of 63%. The combined two steps resulted in the collection of 21.8 mmoles of KHNDA and 4.4 mmoles of NDA. This is equivalent to a 75% molar conversion, and 17% acid purity. The pH of the final filtrate was 8.3.

Example 12

A 1% by weight solution of K2NDA was prepared by mixing 2 mmoles of 2,6 NDA and 4 mmoles of KOH in water. This solution was contacted with $CO_2$ at 700 psig and 25° C. for 2 hours with stirring. After pressure reduction and filtration, 0.0027 mmoles of KHNDA and 1.2 mmoles of NDA were collected. This is equivalent to a molar conversion of 60%, and acid purity of 99.8%. The pH of the filtrate was 7.6.

In contrast to what is observed at high concentrations, at low concentrations the product of the CO2 step is mostly NDA.

Example 13

An experiment similar to that in Example 13, except where the temperature used was 100° C., resulted in 21.4 mmoles of KHNDA and 3.9 mmoles of NDA. This corresponds to a 73% molar conversion.

To maximize conversion per pass with concentrated solutions, it is therefore best to operate at temperatures higher than ambient.

Example 14

A 20% by weight solution of K2NDA was prepared by mixing 35 mmoles of 2,6 NDA and 70 mmoles of KOH in water. This solution was contacted with $CO_2$ at 700 psig and 100° C. for one hour with stirring. Depressuring and filtering produced 25.8 mmoles of KHNDA and 2.5 mmoles of NDA. This corresponds to 81% molar conversion.

Example 15

A 20% by weight solution similar to that described in Example 14 was contacted with $CO_2$ at 700 psig and 150° C. for one hour with stirring. The molar conversion obtained in this experiment was 66%. Increasing temperature beyond 100° C. therefore appears to decrease conversion. This is likely due to enhanced solubility of the disalt at higher temperature.

Example 16

A 15.2% by weight solution of K2NDA similar to that used in Example 10 was contacted with $CO_2$ at the same conditions used in Example 10, except the contact time was only one minute. The molar conversion to the monosalt was 29%. The same experiment was repeated, except the contact time was three minutes. The molar conversion was 67%. The experiment was repeated, except the contact time was increased to eight minutes. The molar conversion was 78%. This is essentially the same as the 75% molar conversion observed in Example 10, when the contact time was one hour.

The contact time in the $CO_2$ step can therefore be very short. About 8 minutes is sufficient to achieve maximum conversion, and five to fifteen minutes is therefore preferred.

Example 17

A 20% by weight solution of K2NDA was prepared by mixing 35 mmoles of 2,6 GNDA and 70 mmoles KOH in water. This solution also contained 5.3 mmoles $K_2CO_3$, for a $CO_3$ to NDA molar ratio of 0.15. Aliquots of this solution were contacted with $CO_2$ at 100° C. for one hour, but at three different $CO_2$ pressures. When the $CO_2$ pressure was 150 psig, the molar conversion observed was 62%. When the $CO_2$ pressure was 300 psig, the molar conversion was 70%. And when the $CO_2$ pressure was 700 psig, the molar conversion was 82%. Filtering at pressure maximizes yield, but with concentrated (5–20%w) solutions it is not a must. Only a fraction of the precipitate redissolves when the pressure is let down.

Increasing $CO_2$ pressure therefore increases conversion.

Example 18

A 5% by weight solution of K2NDA was prepared by dissolving 12 mmoles of K2NDA in water. This solution was contacted with $CO_2$ at 700 psig and 25° C. for one hour. An aliquot of this solution was removed at pressure and titrated with HCl to determine the amount of NDA species remaining in solution. The amount found was nil. The rest of the solution was depressured and filtered. The precipitate obtained represented a 67% molar yield. The filtrate obtained was titrated with HCl and the mmoles of NDA species redissolved by depressuring was found to be 11% of the original NDA in solution. Therefore, if the solution had been filtered at pressure, the molar yield would have been about 78%, instead of the 67% observed after depressuring.

Example 19

A slurry containing 11.1 mmoles of KHNDA and 0.9 mmoles of NDA in 60 g of water was heated at 150° C. for 15 min with stirring. The solid product recovered by filtration consisted of 5.8 mmoles of NDA and 0.03 mmoles of KHNDA. This corresponds to an acid yield of 88% of theory, and an acid purity of 99.5%.

The preferred mode of doing the second step mentioned above (monosalt disproportionation), is therefore at 150° C. for 15 minutes and at monosalt concentration of about 5% by weight.

Example 20

The procedure in Example 19 was repeated, except the slurry contained only 19.5 grams of water. The product was 3.9 mmoles of NDA and 3.2 mmoles of KHNDA. This corresponds to an acid yield of 54% of theoretical, and an acid purity of 55.2%.

An acid product produced by the two-step process contained 0.14% by weight potassium. This material was washed with water at room temperature; filtered and dried. This treatment reduced the potassium content of the product down to 150 ppm.

The purity of the acid produced by the two-step process can therefore be increased by water washing the product.

I claim:

1. A method to recover dicarboxylic or tricarboxylic aromatic acid from salts of such acids, the method comprising the steps of:
   providing an aqueous solution of a salt of a dicarboxylic or tricarboxylic aromatic acid, the aqueous solution having a pH of about 7 or greater;
   contacting the aqueous solution with sufficient carbon dioxide to lower the pH of the aqueous solution resulting in precipitation of at least a portion of the dicarboxylic or tricarboxylic aromatic acid;
   separating precipitated dicarboxylic or tricarboxylic aromatic acid from the solution;
   recovering carbon dioxide from the solution; and
   contacting the separated precipitated dicarboxylic or tricarboxylic aromatic acid with oxalic acid under conditions effective to disproportionate any monosalt of the dicarboxylic or tricarboxylic aromatic acid present to a mixture of disalt and dicarboxylic or tricarboxylic aromatic acid.

2. The method of claim 1, wherein the aqueous solution of a salt of a dicarboxylic or tricarboxylic aromatic acid contains at least five percent by weight of the dicarboxylic or tricarboxylic aromatic acid.

3. The method of claim 1 further comprising the step of contacting the solution from which precipitated dicarboxylic or tricarboxylic acids have separated with carbon dioxide a second time.

4. The method of claim 1 wherein the dicarboxylic or tricarboxylic acid is terephthalic acid.

5. The method of claim 1 wherein the dicarboxylic or tricarboxylic acid is naphthalene dicarboxylic acid.

6. The method of claim 5, wherein the dicarboxylic naphthalene is 2,6 naphthalene dicarboxylic acid.

7. The method of claim 1 wherein the dicarboxylic or tricarboxylic acid is selected from the group consisting of trimesic acid, phthalic acid and isophthalic acid.

8. The method of claim 1 wherein the aqueous solution of a salt of a dicarboxylic or tricarboxylic aromatic acid contains impurities selected from the group consisting of benzoic acid, toluic acid, isophthalic acid, phthalic acid, and mixtures thereof.

9. The method of claim 1 wherein the carbon dioxide is recovered by increasing the temperature of the solution.

10. The method of claim 1 wherein the carbon dioxide is recovered by increasing the temperature and lowering the pressure of the solution.

11. A method to recover dicarboxylic or tricarboxylic aromatic acid from salts of such acids, the method comprising the steps of:
   providing an aqueous solution of a salt of a dicarboxylic aromatic acid selected from the group consisting of phthalic acid, isophthalic acid or of a tricarboxylic aromatic acid, or mixtures thereof, the aqueous solution having a pH of about 7 or greater;
   contacting the aqueous solution with sufficient carbon dioxide to lower the pH of the aqueous solution resulting in precipitation of at least a portion of the dicarboxylic or tricarboxylic aromatic acid;
   separating precipitated dicarboxylic or tricarboxylic aromatic acid from the solution; and
   recovering carbon dioxide from the solution.

12. The method of claim 11, wherein the aqueous solution is an aqueous solution of a salt of a tricarboxylic aromatic acid.

13. The method of claim 12, wherein the tricarboxylic aromatic acid is trimesic acid.

14. The method of claim 11, further comprising the step of contacting the separated precipitated dicarboxylic or tricarboxylic aromatic acid with water under conditions effective to disproportionate at least a portion of any monosalt of the dicarboxylic or tricarboxylic aromatic acid present to a mixture of disalt and dicarboxylic or tricarboxylic aromatic acid.

15. The method of claim 14, wherein the temperature at which the separated precipitated dicarboxylic or tricarboxylic aromatic acid is contacted with water is between about 60° C. and 90° C.

16. The method of claim 11, wherein the aqueous solution of a salt of a dicarboxylic aromatic acid selected from the group consisting of phthalic acid, isophthalic acid or of a tricarboxylic aromatic acid, or mixtures thereof contains impurities selected from the group consisting of benzoic acid, toluic acid, isophthalic acid, phthalic acid, and mixtures thereof.

17. The method of claim 11, wherein the carbon dioxide is recovered by increasing the temperature of the solution.

18. The method of claim 11, wherein the carbon dioxide is recovered by increasing the temperature and lowering the pressure of the solution.

* * * * *